US 7,004,169 B2

(12) United States Patent
Brain

(10) Patent No.: US 7,004,169 B2
(45) Date of Patent: Feb. 28, 2006

(54) LARYNGEAL MASK WITH LARGE-BORE GASTRIC DRAINAGE

(75) Inventor: Archibald I. J. Brain, Les Bons Villers (BE)

(73) Assignee: Indian Ocean Medical Inc., Mahe (SC)

( * ) Notice: Subject to any disclaimer, the term of this patent is extended or adjusted under 35 U.S.C. 154(b) by 0 days.

(21) Appl. No.: 10/981,275

(22) Filed: Nov. 4, 2004

(65) Prior Publication Data

US 2005/0066975 A1    Mar. 31, 2005

Related U.S. Application Data

(63) Continuation of application No. 10/684,048, filed on Oct. 10, 2003, which is a continuation of application No. 09/413,970, filed on Oct. 7, 1999, now Pat. No. 6,631,720.

(51) Int. Cl.
A61M 16/00    (2006.01)

(52) U.S. Cl. ............................ 128/207.14; 128/207.15; 604/96.01

(58) Field of Classification Search ........... 128/207.14, 128/207.15, 207.16, 206.26, 200.26; 604/96.01, 604/174, 912
See application file for complete search history.

(56) References Cited

U.S. PATENT DOCUMENTS

| | | | |
|---|---|---|---|
| 2,862,498 A | 12/1958 | Weekes | |
| 3,554,673 A | 1/1971 | Schwartz et al. | |
| 4,231,365 A | 11/1980 | Scarberry | |
| 4,446,864 A | 5/1984 | Watson et al. | |
| 4,509,514 A | 4/1985 | Brain | |
| 4,553,540 A | 11/1985 | Straith | |
| 4,798,597 A | 1/1989 | Vallincourt | |
| 4,872,483 A | 10/1989 | Shah | |
| 4,953,547 A | 9/1990 | Poole, Jr. | |
| 4,995,388 A | 2/1991 | Brain | |
| 5,038,766 A | 8/1991 | Parker | |
| 5,241,956 A | 9/1993 | Brain | |
| 5,249,571 A | 10/1993 | Brain | |
| 5,282,464 A | * 2/1994 | Brain ..................... | 128/207.15 |

(Continued)

FOREIGN PATENT DOCUMENTS

CA    2067782    6/1999

(Continued)

OTHER PUBLICATIONS

Abdelatti, "A cuff pressure controller for tracheal tubes and larngeal mask airway," *Anaesthesia*, (1999) 54:981-986.

(Continued)

*Primary Examiner*—Teena Mitchell
(74) *Attorney, Agent, or Firm*—Wilmer Cutler Pickering Hale and Dorr LLP

(57) ABSTRACT

An artificial airway device for use in unconscious patients comprises a laryngo-pharyngeal mask including an expandable masking ring. The expandable mask sealingly surrounds the laryngeal inlet when expanded to obstruct communication between the laryngeal inlet and oesophagus. One or more airway tubes connected to the mask provide for fluid flow to a portion of the mask facing the laryngeal inlet when said mask sealingly surrounds the laryngeal inlet. A gastro-tube connected to the mask provides a fluid flow-path to the mask when the mask sealingly surrounds the laryngeal inlet. The distal end of the gastro tube passes through the masking ring at its narrower distal region where, when installed in a patient, it abuts against the oesophagus; and the distal portion of the gastro-tube flattens when the mask is deflated to facilitate smooth passage behind the larynx during insertion through the mouth and throat of the patient.

7 Claims, 6 Drawing Sheets

U.S. PATENT DOCUMENTS

| | | | |
|---|---|---|---|
| 5,297,547 A | 3/1994 | Brain | |
| 5,303,697 A | 4/1994 | Brain | |
| 5,305,743 A | 4/1994 | Brain | |
| 5,339,805 A | 8/1994 | Parker | |
| 5,339,808 A | 8/1994 | Don Michael | |
| 5,355,879 A | 10/1994 | Brain | |
| 5,391,248 A | 2/1995 | Brain | |
| 5,529,582 A | 6/1996 | Fukuhara | |
| 5,569,219 A | 10/1996 | Hakki et al. | |
| 5,584,290 A * | 12/1996 | Brain | 128/207.15 |
| 5,599,301 A | 2/1997 | Jacobs et al. | |
| 5,623,921 A * | 4/1997 | Kinsinger et al. | 128/200.26 |
| 5,632,271 A | 5/1997 | Brain | |
| RE35,531 E * | 6/1997 | Callaghan et al. | 128/207.15 |
| 5,653,229 A | 8/1997 | Greenberg | |
| 5,655,528 A | 8/1997 | Pagan | |
| 5,682,880 A | 11/1997 | Brain | |
| 5,711,293 A | 1/1998 | Brain | |
| 5,743,254 A | 4/1998 | Parker | |
| 5,746,202 A | 5/1998 | Pagan | |
| 5,771,889 A | 6/1998 | Pagan | |
| 5,791,341 A | 8/1998 | Bullard | |
| 5,850,832 A | 12/1998 | Chu | |
| 5,865,176 A | 2/1999 | O'Neil | |
| 5,878,745 A | 3/1999 | Brain | |
| 5,881,726 A | 3/1999 | Neame | |
| 5,896,858 A | 4/1999 | Brain | |
| 5,915,383 A | 6/1999 | Pagan | |
| 5,937,860 A | 8/1999 | Cook | |
| 5,979,445 A | 11/1999 | Neame et al. | |
| 5,983,897 A | 11/1999 | Pagan | |
| 5,988,167 A * | 11/1999 | Kamen | 128/207.15 |
| 6,003,510 A | 12/1999 | Anunta | |
| 6,003,514 A | 12/1999 | Pagan | |
| 6,012,452 A | 1/2000 | Pagan | |
| 6,021,779 A * | 2/2000 | Pagan | 128/207.15 |
| 6,050,264 A | 4/2000 | Greenfield | |
| 6,070,581 A | 6/2000 | Augustine et al. | |
| 6,079,409 A | 6/2000 | Brain | |
| D429,811 S | 8/2000 | Bermudez | |
| 6,095,144 A | 8/2000 | Pagan | |
| 6,116,243 A | 9/2000 | Pagan | |
| 6,119,695 A | 9/2000 | Augustine et al. | |
| 6,390,093 B1 | 5/2002 | Mongeon | |
| 6,631,720 B1 * | 10/2003 | Brain | 128/207.14 |

FOREIGN PATENT DOCUMENTS

| | | |
|---|---|---|
| CA | 2012750 | 8/1999 |
| EP | 0 389 272 | 9/1990 |
| EP | 0 402 872 | 12/1990 |
| EP | 0 294 200 | 4/1992 |
| EP | 0 580 385 | 1/1994 |
| EP | 0 712 638 | 5/1996 |
| EP | 0 732 116 | 9/1996 |
| EP | 0 796 631 | 9/1997 |
| EP | 0 845 276 | 6/1998 |
| EP | 0 865 798 | 9/1998 |
| EP | 0 922 465 | 6/1999 |
| EP | 1 125 595 | 8/2001 |
| GB | 2111394 | 7/1983 |
| GB | 2205499 | 12/1988 |
| GB | 2317342 | 3/1998 |
| GB | 2317830 | 4/1998 |
| GB | 2318735 | 5/1998 |
| GB | 2319478 | 5/1998 |
| GB | 2321854 | 8/1998 |
| GB | 2323289 | 9/1998 |
| GB | 2323290 | 9/1998 |
| GB | 2323291 | 9/1998 |
| GB | 2323292 | 9/1998 |
| GB | 2359996 | 9/2001 |
| JP | 10263086 | 10/1996 |
| JP | 10118182 | 5/1998 |
| JP | 10216233 | 8/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO 91/03207 | 3/1991 |
| WO | WO 91/07201 | 5/1991 |
| WO | WO 91/12845 | 9/1991 |
| WO | WO 92/13587 | 8/1992 |
| WO | WO 95/33506 | 12/1995 |
| WO | WO 97/12640 | 4/1997 |
| WO | WO 97/12641 | 4/1997 |
| WO | WO 98/16273 | 4/1998 |
| WO | WO 99/06093 | 2/1999 |
| WO | WO 00/22985 | 4/2000 |
| WO | WO 00/23135 | 4/2000 |
| WO | WO 00/61212 | 10/2000 |

OTHER PUBLICATIONS

Benumof J.L., "Management of the difficult adult airway with special emphasis on awake trachael intubation," *Anesthesiol.* (1991). 75(6):1087-1110.

Benumof, "Laryngeal Mask Airway and the ASA Difficult Airway Algorithm," *Anesthesiology* (1996) 84(3):686-99.

Bernhard, et al., "Adjustment of Intracuff Pressure to Prevent Aspiration," *Anesthesiology* (1979) 50(4):363-366.

Bernhard, et al., "Physical Characteristics of and Rates of Nitrous Oxide Diffusion into Technical Tube Cuffs," *Anesthesiology* (1978) 48:413-417.

Brain, et al., "A new laryngeal mask prototype," *Anaesthesia*, (1995) 50:42-48.

Brain, "The laryngeal mask airway," *Anaesthesia*, (1985) 40:356-361.

Brain, "Three cases of difficult intubation overcome by the laryngeal mask airway," *Anaesthesia*, (1985) 40:353-355.

Brain, "The Laryngeal Mask Airway—A Possible New Solution to Airway Problems in the Emergency Situation," *Archives of Emergency Medicine*. (1984) 1:229-232.

Brain, "The Laryngeal Mask—A New Concept in Airway Management," *Br. J. Anesth.* (1983) 55:801-805.

Brimacombe, "The split laryngeal mask airway," p. 639.

Broderick, "The laryngeal mask airway," *Anaesthesia*, (1989) 44:238-241.

Burgard, et al., "The Effect of Laryngeal Mask Cuff Pressure on Postoperative Sore Throat Incidence," *J. of Clinical Anesthesia* (*1996*) 8:198-201.

Caplan, et al., "Adverse respiratory events in anesthesia: a closed claims analysis", *Anesthesiol.* (1990) 72:828-833.

Craven, "Prevention of Hospital-Acquired Pneumonia: Measuring Effect in Ounces, Pounds, and Tons," *Annals of Internal Medicine*, (1995) 122(3):229-231.

Cuff-Pressure-Control CDR 2000, LogoMed.

Davies, et al., "Laryngeal Mask Airway and Tracheal Tube Insertion by Unskilled Personnel", The Lancet, 336:977-979.

DeMello, et al., "The use of the laryngeal mask airway in primary anaesthesia," *Anaesth. Corresp.* (1990) 45(9):793-794.

Doyle et al., "Intraoperative Awareness: A Continuing Clinical Problem," http://doyle.lbme.utoronto.ca/anesthesia/aware.htm.

Engbers, "Practical use of 'Diprifusor' systems", *Anaesthesia* (1998), 53, Suppl. 1, pp. 28-34.

Eriksson, et al., "Functional Assessment of the Pharynx at Rest and during Swallowing in Partially Paralyzed Humans," *Anesthesiology* (1997) 87(5):1035-1042.

Glen, "The development of 'Diprifusor': a TCI system for propofol," *Anaesthesia* (1998), 53, Suppl. 1, pp. 13-21.

Gray et al., "Development of the technology for 'Diprifusor' TCI systems," *Anaesthesia* (1998), 53, Suppl. 1 pp. 22-27.

Heath, "Endotracheal intubation through the Laryngeal Mask—helpful when laryngoscopy is difficult or dangerous," *European Journal of Anaesthesiology* (1991), Suppl. 4:41-45.

Hickey, et al., "Cardiovascular Response to Insertion of Brain's Laryngeal Mask", Anaesthesia, (1990) 45:629-633.

Inomata, et al., "Transient Bilateral Vocal Cord Paralysis after Insertion of a Laryngeal Mask Airway," *Anesthesiology*, (1995) 82:787-788.

Jacobson et al., A Study of Intracuff Pressure Measurements, Trends and Behaviours in Patients During Prolonged Periods of Tracheal Intubation, *Br. J. Anaesth.* (1981) 53, 97-101.

Kambic, et al., "Intubation Lesions of the Larynx," *Br. J. Anasth.* (1978) 50: 587-590.

Kapila, et al., "Intubating laryngeal mask airway: a preliminary assessment of performance", *British Journal of Anaesthesia*, (1995) 75:228-229 (Abstract).

Lindholm, "Prolonged Endotracheal Intubation," *ACTA Anaesthesiologica Scandinavica* (1969) 33:32-46.

Majumder, et al., "Bilateral Lingual Nerve Injury Following the Use of the Laryngeal Mask Airway," *Anaesthesia*, (1998) 53:184-186.

Miller, "A pressure regulator for the cuff of a tracheal tube," *Anaesthesia*, (1992) 47:594-596.

Muthuswamy, et al., "The Use of Fuzzy Integrals and Bispectral Analysis of the Electroencephalogram to Predict Movement Under Anesthesia," *IEEE Transactions on Biomedical Engineering*, (1999) 46(3):290-299.

Nagai, "Unilateral hypoglossal nerve paralysis following the use of the laryngeal mask airway," *Anaesthesia*, (1994) 49:603-604.

Patel, et al, "Trachael tube cuff pressure," *Anaesthesia*, (1984) 39:862-864.

Pennant, "Comparison of the Endotracheal Tube and Laryngeal Mask in Airway Management by Paramedical Personnel," *Anesth Analg* (1992) 74:531-534.

Pippin, et al., "Long-term tracheal intubation practice in the United Kingdom", *Anaesthesia*, (1983) 38:791-795.

Raeder, et al., "Tracheal tube cuff pressure," *Anaesthesia*, (1985) 40:444-447.

Seegobin, et al., "Endotracheal cuff pressure and tracheal mucosal blood flow: endoscopic study of effects of four large volume cuffs," *British Medical Journal*, (1984) 288: 965-968.

Willis, et al., "Tracheal tube cuff pressure," *Anaesthesia*, (1988) 43:312-314.

Worthington, et al., "Performance of Vaporizers in Circle Systems (l)," *Br. J. of Anaesthesia* (1995) 75:228P-229P.

Wynn, et al., "Tongue Cyanosis after Laryngeal Mask Airway Insertion," *Anesthesiology*, (1994) 80(6):1403.

* cited by examiner

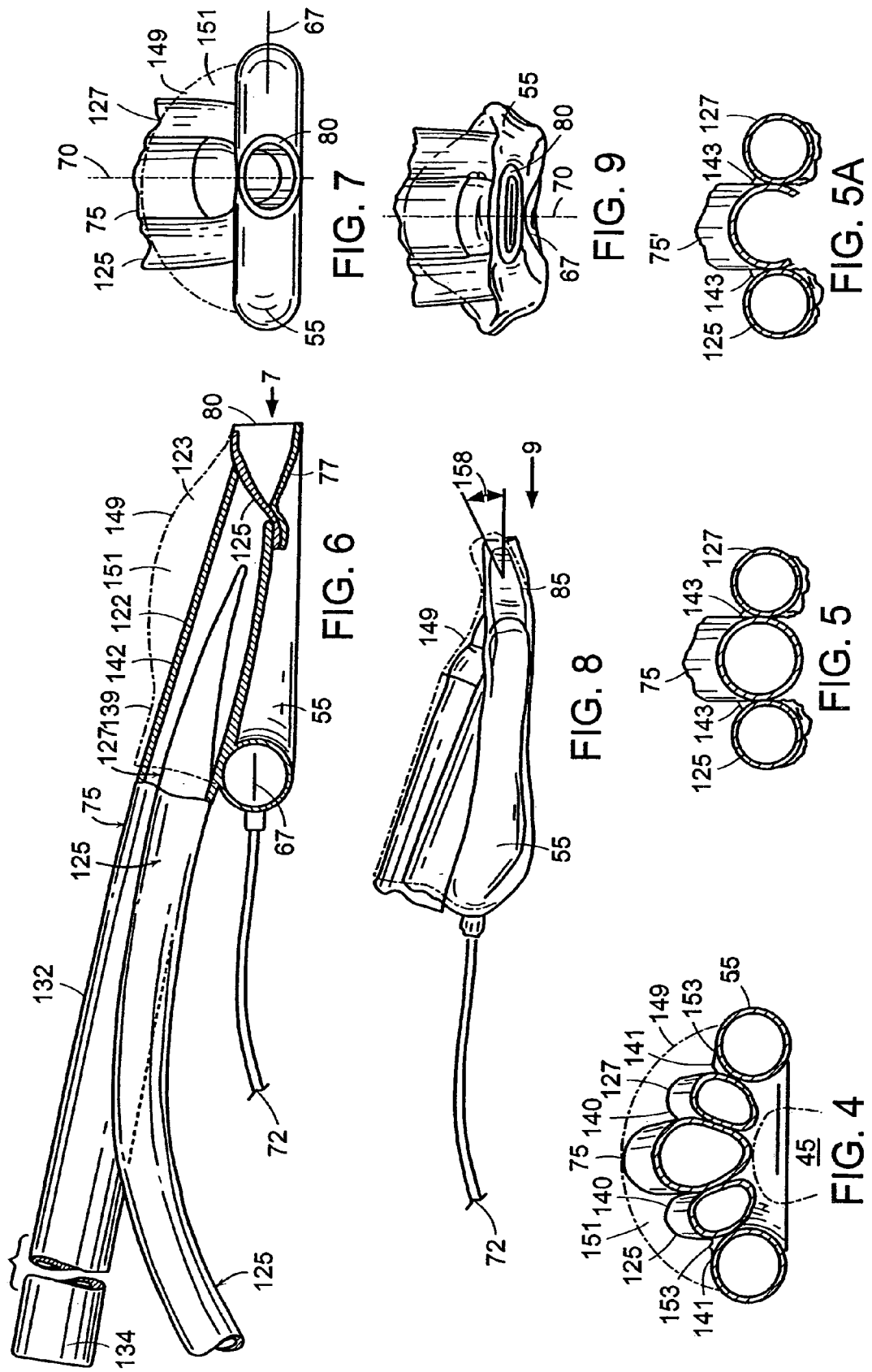

LARYNGEAL MASK WITH LARGE-BORE GASTRIC DRAINAGE

CROSS REFERENCE TO RELATED APPLICATIONS

This application is a continuation of application Ser. No. 10/684,048, filed Oct. 10, 2003, which is a continuation of application Ser. No. 09/413,970, filed Oct. 7, 1999, now U.S. Pat. No. 6,631,720.

BACKGROUND OF THE INVENTION

The present invention relates generally to medicine, and more particularly, to anesthesia, emergency medicine, intensive therapy, and veterinary medicine.

The laryngeal mask airway (LMA) disclosed in U.S. Pat. No. 4,509,514 is an artificial airway device designed to facilitate ventilation of an unconscious patient, and is used in over 80 countries. An unconscious patient, undergoing ventilation whether spontaneous or controlled via an LMA, may regurgitate or vomit gastric contents, as may happen if the stomach is not empty before such ventilation. Leakage of such gastric contents into the lungs should be prevented because it may be fatal. U.S. Pat. No. 5,241,956 describes modified laryngeal masks including a tube for entry into the oesophagus (i.e., gullet) to drain liquid gastric contents therefrom. A laryngeal mask including a drainage tube for extraction of gastric drainage is also disclosed in U.S. Pat. No. 5,632,271.

Providing a laryngeal mask which retains the ease of use of the original but also has a tube for drainage of gastric contents, may be difficult. Additionally, installation in a patient of a laryngeal mask having a large-bore gastric drainage tube (e.g., as described in U.S. Pat. No. 5,241,956) may be more difficult as compared to a standard LMA device. Also, while a laryngeal mask having a smaller-bore gastric drainage tube is typically easier to install in a patient, the flow capacity of such a drainage tube for gastric contents (resulting, for example, from vomiting) may be more limited. Moreover, a laryngeal mask having a smaller-bore gastric drainage tube may not be able to accommodate a large stomach tube (e.g., of greater than 6 mm OD).

The disclosures of all of the above referenced patents are hereby incorporated by reference.

DEFINITION OF TERMS

As used herein, the anatomical terms "anterior" and "posterior," with respect to the human body, refer to locations nearer to the front of and to the back of the body, respectively, relative to other locations. The anatomical terms "proximal" and "distal," with respect to the human body, refer to locations nearer to the outside of and to the inside of the body, respectively, relative to other locations. The term "lateral" refers to a location to the right or left sides of the body, relative to other locations. "Bilateral" refers to locations both to the left and right of the body, relative to other locations. The anatomical term "medial" or "medially" refers to a location toward the center or midline of the body, relative to locations both to the left and right of the body.

BRIEF STATEMENT OF THE INVENTION

It is an object of the invention to provide a laryngeal mask for humans and other mammals which offers ease of insertion, and in addition accommodates a large-bore "gastro-tube", typically larger than the airway tube(s) of the device and up to 15-mm inside diameter in adult human sizes. In the event of reflux of gastric contents, the larger-bore tube permits substantially unobstructed passing of such matter from the oesophagus to the exterior of the mouth. Also, a large-bore drainage tube may be used as a conduit for other applications such as temperature monitoring, endoscopy, suction or alimentation, which may be accommodated through a gastro-tube.

It is a further object to provide a gastric drain tube that is collapsible at its distal end to facilitate device insertion, but that, when the device is installed and inflated, tends to become open as permitted by the anatomy.

An object of preferred aspects of the present invention is to arrange the airway and gastro-tube features so as to reduce the bulk and stiffness of the LMA structure thereby to increase the tolerance by the patient of the LMA, and facilitate insertion of the LMA into the patient; and to simplify the LMA structure.

Other objects of preferred aspects are to provide an LMA that secures continuous airway accommodation of the patient, and that optionally may provide further functions such as adjustable-rate removal of waste gases by reduction in the so-called dead space or space not contributing to gas exchange, unobstructing guidance of an insertable inspection or manipulating device within the airway, avoidance of any epiglottic obstruction to passage of gases to and from the lungs, and avoidance of obstruction of the gastric drain tube by compression from surrounding anatomical structures.

In a preferred embodiment, the invention achieves the foregoing objects and provides further advantageous features in an LMA construction wherein a large-bore gastro-tube is integrated with an inflatable/deflatable masking ring which provides an LMA seal around the laryngeal inlet and with adjacent independent airway supply to the patient's lungs, and in which the prior art requirement for a backing plate is avoided. A gastro-tube is externally and tangentially bonded to a first, more proximal, region of the inflatable/deflatable masking ring as it traverses the same. The gastro-tube is also bonded to a second and more distal region of the inflatable/deflatable masking ring, and has externally sealed passage through wall portions of the distal region of the inflatable/deflatable masking ring to a distally open end, such that gastric drainage is provided at substantially the distal limit of the masking ring.

For embodiments providing independent airway-supply, two flexible tubes are bonded along opposite sides of the gastro-tube at least in the course of traversing the first more proximal region and continuing to the point of first intercept with the second more distal region of the masking ring. In some embodiments, the airway tubes and gastro-tube are sealed to each other to create an external cover for the interior space of the mask, thus enabling bonded masking closure of the space within the annulus of the inflatable masking ring by continuous bonding of the masking ring to adjacent wall structure of the airway tubes. In some embodiments, apertures for airway communication through the thus-formed masking closure are provided as slotted laterally open features of the airway tubes, on the anterior or larynx-exposed side of the masking closure; and the distal ends of the like airway tubes are cut diagonally to form twin gutters with distally pointed ends, the concavity of the gutters facing the laryngeal opening.

The employment of two airway tubes enables various optionally available further features, as follows:

(a) The indicated aperturing of both airway tubes in the region of the masking-closure enables dual airways to serve the patient's lungs, the combined cross-section areas offering lower airway resistance and stiffness then would a single tube having the same total size.

(b) Alternatively, one of the airway tubes can provide for gas flow unidirectionally to the lungs; and the other tube may serve to output expired gases, thus greatly facilitating removal of; e.g., the waste gas carbon dioxide;

(c) External connection of one airway tube to an air or gas supply and the other airway tube to an evacuation system enables continuous supply of fresh air and extraction of waste air or gas; and (d) Sealing of the gastro-tube to the inflatable masking ring that provides LMA-sealed airway service to a patient, as in the preferred embodiment of the invention disclosed herein below, ensures effective separation of the gastrointestinal and respiratory tract and, optionally, permits truncation of the gastro tube proximal to the cuff but distal to the teeth, thus enabling the gastro-tube to not extend far enough to pose a problem of passage through the teeth of a patient, for example when the openable distance between the teeth is restricted by disease or anatomical factors.

Other advantages and features of various aspects of the invention will appear in the course of the accompanying detailed description.

BRIEF DESCRIPTION OF THE DRAWINGS

FIG. 4 is an enlarged cross-section, in the plane indicated by the line 4—4 of FIG. 3, showing the gastro-tube and airway gutters, the masking ring and posterior cover being shown in the inflated condition.

FIG. 5 is a cross-section similar to FIG. 4, in the plane indicated by the line 5—5 of FIG. 3, proximally of the masking ring, showing the airway tubes, and gastro-tube.

FIG. 5A is a cross-section similar to FIG. 4, in the plane indicated by the line 5—5 of FIG. 3, proximally of the masking ring, showing the airway tubes, and an alternative embodiment gastro-tube.

FIG. 6 is a side view in partial section, in the plane indicated by the line 6—6 of FIG. 3, part of which coincides with the central medial plane of symmetry, showing the masking ring and posterior cover in the inflated condition.

FIG. 7 is an elevational end view in the direction 7 of FIG. 6, showing the cross-sectional shape of the gastro-tube for the inflated condition of the masking ring.

FIG. 8 is a side view in the direction 8 of FIG. 3 for the deflated condition of the masking ring, the distal region of masking ring also being shown in phantom in a partially deflected condition.

FIG. 9 is an elevational end view in the direction 9 of FIG. 8, showing the cross-sectional shape of the gastro-tube for the deflated condition of the masking ring.

Corresponding reference characters indicate corresponding parts throughout the several views of the drawings.

DETAILED DESCRIPTION

Figure 1:
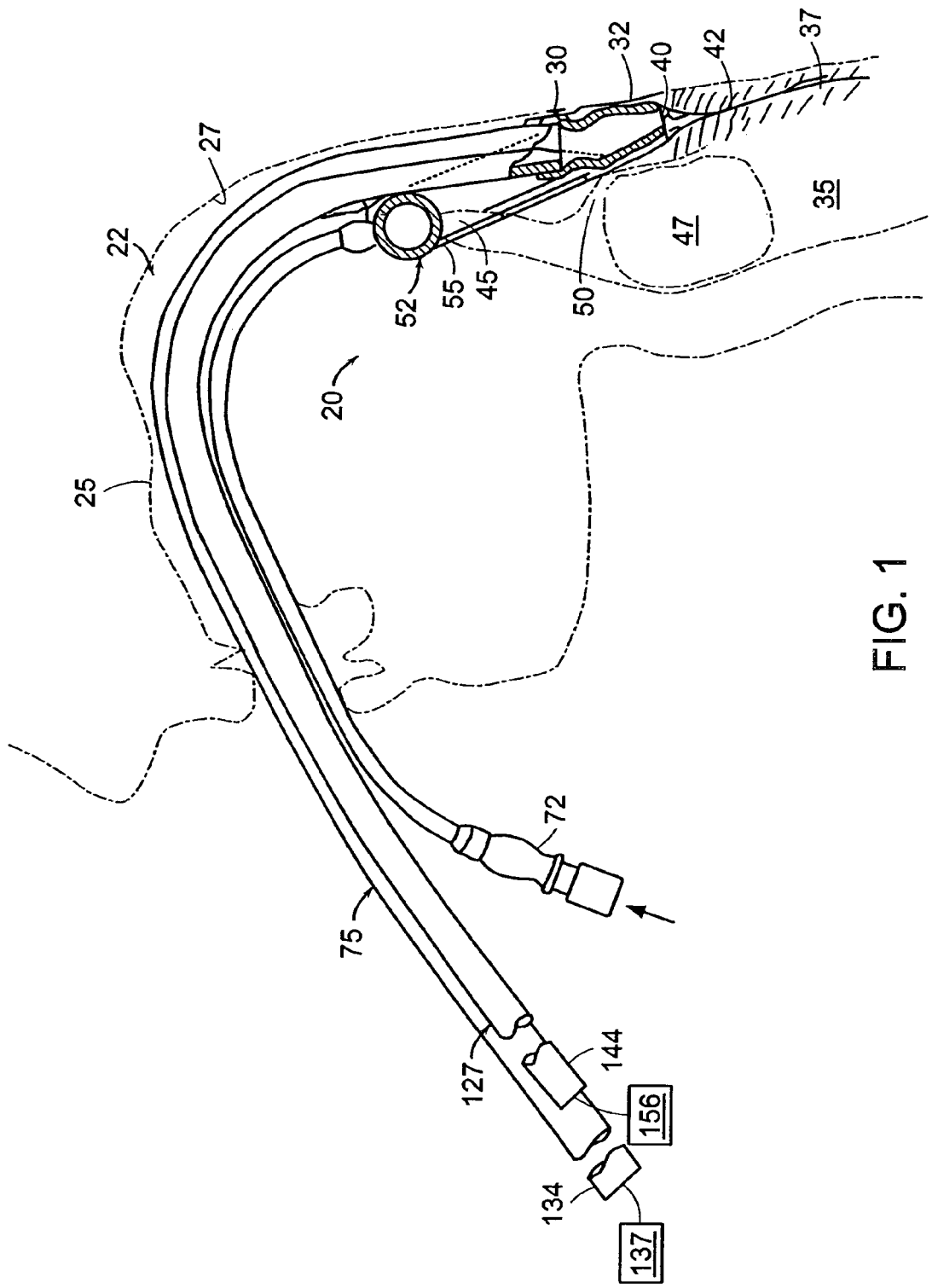
FIG. 1 is a simplified overall view to show a device of the invention, installed in a patient whose coacting anatomical features are suggested by phantom outlines, the left portion of the distal region of the masking ring and the adjacent portion of the left airway tube being broken away to better show the connection between the gastro tube lip and the masking ring.

A laryngeal-mask airway system embodying the present invention is designated generally by the reference numeral 20 in FIG. 1.

As discussed in more detail below, airway system 20 includes a mask structure 52 at the distal ends of a flexible gastro-tube 75 and a pair of airway tubes 125, 127. The gastro-tube and airway tubes conform to the curvature of the patient's airway when flexed. The proximal end 134 of gastro-tube 75 may be connected to a conventional, external gastro suction apparatus 137. The proximal tube 144, 147 of airway tubes may be connected to a conventional ventilating system 156 external of the patient. Air inflation/deflation tube 72 also passes from external of the patient and through the patient airway to the mask structure.

Airway system 20 is inserted into anatomical airway 22 the upper surface of which is bounded by hard and soft palates 25, 27. The mask 52 of airway system 20 is lodged in pharynx 30 of anatomical airway 22 at the base of hypopharynx 32 where the airway divides into trachea 35 (i.e., windpipe) and oesophagus 37. A lower portion of airway system 20 extends to sealing engagement with the upper oesophageal sphincter.

Masking Ring

Figure 2:
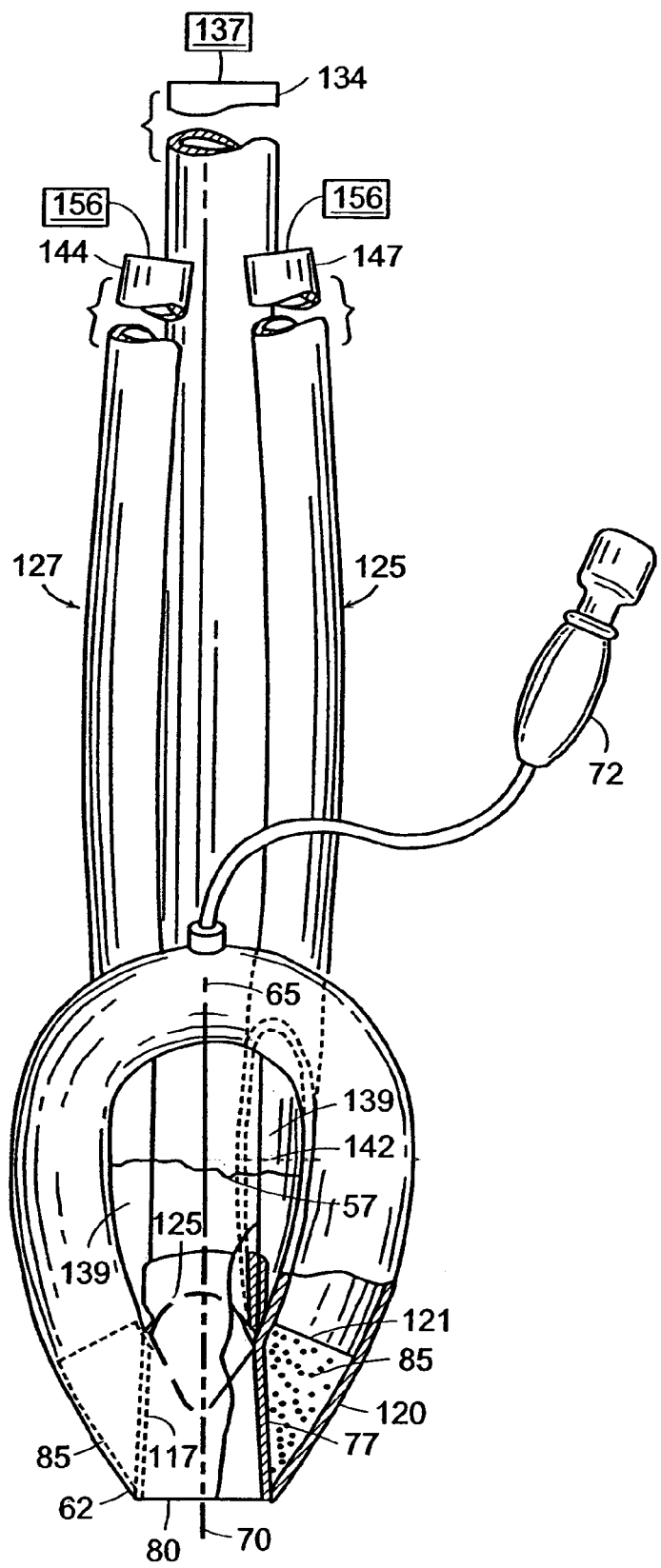
FIG. 2 is a plan view of the anterior side of the device of FIG. 1, the masking ring being in inflated condition on an enlarged scale relative to FIG. 1, a portion of the gastro-tube being shown broken away to reveal the connection between its lip and the masking ring.
Figure 3:
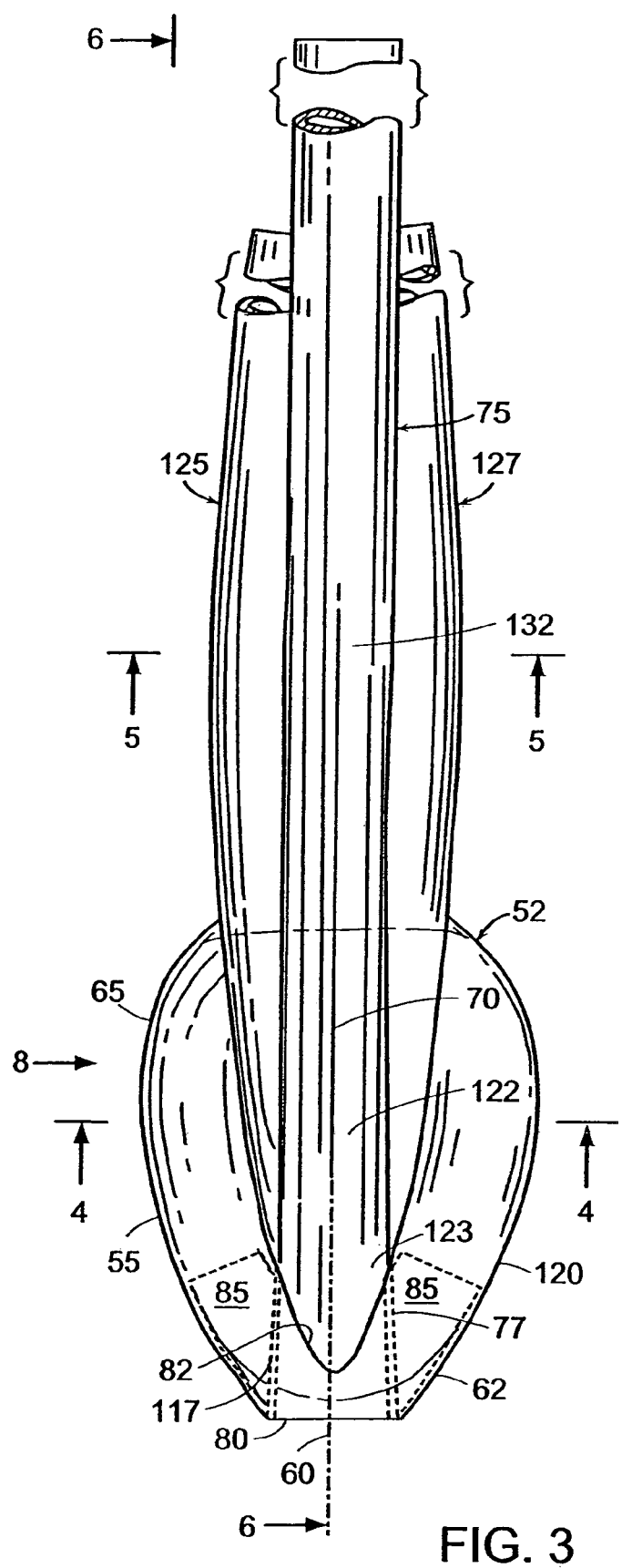
FIG. 3 is a plan view of the posterior side of the device of FIG. 2 in the same inflated condition, to the scale of FIG. 2, showing the posterior cover in transparent phantom to reveal the external connection between the gastro tube lip and the masking ring.

Mask 52 comprises a generally elliptical inflatable/deflatable masking ring or sealing cushion 55, the proximal portion 65 of which is attached to the distal end of inflation tube 72. The periphery of masking ring 55 is closed thereby defining an inner space bowl 57 between its transversely spaced walls. Masking ring 55 has a major axis 60 extending between its distal and proximal regions 62, 65, as shown in FIGS. 2 and 3. Masking ring 55 establishes a geometric first plane 67 of anterior/posterior symmetry (also conveniently referred to as an equatorial plane) containing the locus of cross-sectional centers of the masking ring. Equatorial first plane 67 also includes major axis 60. Masking ring 55 further establishes a geometric medial second plane 70 of lateral symmetry that also includes major axis 60 and that is perpendicular to equatorial first plane 67. The distal region 62 of masking ring 55 is narrower than proximal region 65 in first plane 67, as shown in FIGS. 2 and 3.

Masking ring 55 may conveniently be made from silicone with a typical wall-thickness of approximately 0.5 to 1 mm but thinner walls may be suitable for enhanced sealing capability, for example 0.1–0.3 mm. Masking ring 55 may alternatively be made of, or may be filled with, cellular material.

The somewhat wider transverse diameter of the inner space 57 of masking ring 50, in relation to the aryepiglottic folds, is sufficient to accommodate the large-bore gastro-tube 75 without obstructing gas access to and from laryngeal inlet 50. Gastro-tube 75 is placed in bisecting longitudinal relation of the major axis 60 of masking ring 55 such that, when installed in the patient, epiglottis 45 may be supported against the anterior surface of the gastro-tube in bowl 57.

In the disclosed embodiment, the anteriorly-facing surface of the cushion of masking ring 55 is generally elliptical and, when the masking ring is in place, may deform as required to provide the desired anatomical seal. Optionally, soft and yielding ridges (not shown) may be bilaterally disposed on the anteriorly-facing distal region 62 of the generally elliptical-shaped cushion of masking ring 55, over an area corresponding generally to about one-half of the total longitudinal extent of the masking ring, to fit into the anatomical grooves (e.g. the pyriform fossae) disposed on either side of the glottis. To increase the pressure of the masking ring against the anatomic structures to which it is sealed, the generally elliptical cushion of masking ring 55 optionally may also include a second wedge-shaped horseshoe-like crescent (not shown) of similar elastic hollow material, mounted on the anterior surface of substantially the proximal one-half of the masking ring which includes proximal region 65, to increase the pressure with which the mask is urged into position surrounding the laryngeal inlet. The thinner edge of such a wedge-shaped crescent is directed distally, i.e., towards the more pointed distal region 62 of masking ring 55, so enhancing the anterior-posterior depth of the masking ring progressively towards its wider proximal region 65.

Masking ring 55 is adapted for placement in anatomical airway 22 such that inner space 57 surrounds laryngeal inlet 50 of the patient. Masking ring 55 may then be inflated through inflation tube 72 connected to the masking ring. Masking ring 55, when so positioned and inflated, sealingly engages the tissues surrounding laryngeal inlet 50, described more fully herein below.

Gastro-tube

Gastro-tube 75 generally bisects the space between the proximal and distal regions 65, 62 of masking ring 55. Throughout most of its length, gastro-tube 75 may conveniently be molded or extruded from a flexible or elastomeric material such as silicone or other plastic or rubber, preferably of durometer hardness in the range 50 to 80 Shore. For use in adult humans, the inner diameter (i.d.) of gastro-tube 75 may be about 10 to 15 mm, and the radial wall thickness may be about 1 to 2 mm.

The distal portion of gastro-tube 75 comprises a relatively short, more flexible and, typically, thinner-walled and more easily flattened tube, which is bonded to distal end of the major length (e.g., the portion 122 of the gastro tube which is generally within the mask 55 and the portion 132 of the gastro tube which is proximal to mask 55) of the gastro-tube and provides a lip portion 77. The distal end of lip tube 77 defines an open distal end 80 which, when masking ring 55 is inserted via the anatomical airway 22 of the patient into position opposite laryngeal inlet 50, communicates with the oesophageal inlet. The center of distal end 80 coincides with the axis of intersection between first and second planes 67, 70, as shown in FIGS. 7 and 9, and portion of the gastro tube proximal of lip portion 77 slopes posteriorly at an angle of about 30.

Lip portion tube 77 including distal end 80 extends through the distal region 62 of masking ring 55, and is sealed to ring 55 at both its proximal entrance into and distal exit from the distal region of the ring. To enable lip portion tube 77 to so extend through distal region 62, two openings are provided on, respectively, the distal and proximal sides of crotch portion 82 of distal region 62, as shown in FIGS. 2 and 3. These openings in the inflatable tube of masking ring 55 are closed by peripherally sealing the edges of the openings to the periphery of lip portion 77. As shown most clearly in FIG. 6, the proximal end of lip portion tube 77 extends into the bowl or interior space 57 of the masking ring 55, and the proximal end of the lip portion tube is closed by sealing the end edges together.

For attachment to lip portion tube 77, the distal end of portion 122 of gastro tube 75 is cut at an angle to the central axis of the gastro tube, providing a distal pointed nib 123 and an anteriorly facing elongated opening 125. The configuration of nib 123 is such that, as shown in FIG. 3, the tip passes through an opening in the adjacent posterior, inner side of the distal end portion of masking ring 55, and is bonded to the masking ring 55. The edges of opening 125 at the distal end of backing portion 122, and the anterior side of backing portion adjacent the opening are similarly bonded to the posterior side of lip portion tube 77. To provide continuous communication between lip portion 77 and the remaining portions of gastro tube 75, the region of the lip portion tube 77 within the bounds of opening 125 is removed for flow between lip portion 77 and gastro tube portion 122.

When masking ring 55 is deflated, the cross-section of distal end 80 of lip portion 77 is flattened in equatorial first plane 67, as shown in FIG. 9, to a slit, or to a nearly closed "fish-mouth" shape. The cross section of the more proximal section of lip portion 77 progressively becomes less flattened and more nearly circular along the longitudinal axis of gastro tube 75 toward portion 122 of the tube, that, as discussed in more detail hereafter, forms part of backer portion surface of bowl 57. Inflation of distal region 62, distal end 80 becomes less flattened and more nearly circular, similar to the remaining proximal section of lip portion 77 and to the remaining length of gastro tube 75, as shown in FIG. 7.

It thus will be seen that airway system 20 provides a device whereby the distal or innermost-reaching end 80 of the large-bore gastro-tube 75 may change its transverse configuration from a relatively closed, anterior-posteriorly flattened wedge-shaped slit when the sealing component (i.e.; cushion or masking ring) device is in its flattened or reduced volume state for insertion into a human patient, towards a relatively open, e.g. an oval or roughly circular opening, when the device is installed in the human or animal patient and the sealing mask is expanded, particularly in response to the opening of the adjacent oesophageal sphincter which engages the distal end of the mask. The inflation pressure of the masking ring is typically chosen so that the force tending to open the lips is too low to force the anatomy open in normal circumstances, but is strong enough to open the lips to receive gastric contents if the anatomy itself relaxes as during the process of reflux or vomiting. The reason for this arrangement is that if these lips are always fully to open during mask inflation, this could tend to force the sphincter of the oesophagus to open as well, an undesirable effect. In the embodiment in which the generally elliptical masking ring 55 is made of a hollow flexible material, the mask is typically inflated using an external inflation device 72, e.g., a syringe which may also be used to deflate the mask when so desired.

When mask is inflated as shown in FIG. 7 and distal aperture 80 is in its open configuration, distal aperture 80 typically is generally elliptical, having a transverse or horizontal I.D. dimension (of about 1.5 cm. in a device designed for an adult human) that is typically about one and a half times its vertical dimension (of about 1 cm in an adult device). When masking ring 55 is deflated as shown in FIG. 9, this vertical dimension is substantially flattened, and the horizontal dimension is increased. The maximum width of the deflated masking ring in the region of the laryngeal inlet is limited by the anatomical structure of the hypopharynx on either side of the inlet; i.e., the flattened distal end of the masking ring should properly fit into position. Proximally of distal aperture 80, the transverse or horizontal dimension of lip portion 77 may decrease along its longitudinal axis in the proximal direction such that the cross section of the lip portion ultimately becomes more circular. It will be noted that the cross-sectional area of the aperture, when open, may be greater than that of proximal portions of the gastro tube.

For controlling the opening (during use) and closing (during insertion) of distal aperture 80, a pair of generally circular in cross-section, wedged-shaped distal support plugs 85 are lodged in the inside of distal region 62 of masking ring 55. A support plug 85 is provided on each of the diametrically opposite sides of lip portion 77 of gastro-tube 75, between the gastro tube and the inner surface of distal region 62, as shown in FIGS. 2 and 3. The outer and generally cylindrical surface 120 of each support plug abuts (and typically is sealed to) the inner surface of the distal region 62 of masking ring 55 adjacent the gastro tube lip portion 77 (or, alternatively, the thin-sleeved passage) extending through the distal region. The distal end 117 of each support plug 85 is sealed to the outer peripheral surface of lip portion 77 of gastro tube 75 (or, and again alternatively, to the thin sleeved passage). As will be appreciated, the distal end of each plug is typically concave and conforms to the outer and generally elliptical or circular surface of lip portion (or of the sleeve) to which it is sealed.

Each support plug 85 is formed of a sponge-like, open-cell or air-permeable, material. When masking ring 55 is deflated by substantial evacuation of the interior of masking ring 55 through tube 76, the deflation causes the distal support plugs 55 to be substantially flattened. On inflation of masking ring 55, the distal plugs expand, support the sides of thin-walled lip portion 77 to which they are attached, and prevent the air pressure within the masking ring from collapsing the thin-walled portion. It will be noted that in embodiments in which the distal ends 117 of the plugs are themselves sealed, the plug ends themselves may form at least a portion of lip portion to be 77.

Backing portion 122 of gastro tube 75, proximal to the lip portion 77, extends between lip portion 77 and proximal region 65 of masking ring 55. Typically, the cross section of backing portion 122 is substantially more resistant to flattening than is lip portion 77; and the intermediate region of backing portion 122 preferably has a pear shaped or tear-drop shaped cross section, where the apex of the pear or tear-drop cross-section faces anteriorly relative to the equatorial first plane 67. Less preferably, backing portion 122 of gastro-tube 75 between distal and proximal regions 30, 28 may have more elliptical or semi-elliptical cross section.

Gastro-tube 75 is bonded tangentially to the proximal region 65 of masking ring 55 on the posterior side thereof such that the axis of the backing portion 122, like that of lip portion 77, is contained in medial second plane 70. The tube 75 thus is posteriorly offset relative to equatorial first plane 67 of the elliptical masking ring 55 such that, in proximal region 65, the gastro-tube 75 passes tangential and posterior to the generally circular cross-section of the inflatable masking ring. The cross-section of backing portion 22 is substantially circular where it is bonded in posterior tangential contact with the proximal region 65 of masking ring 55.

Proximal to the portion thereof having a pear- or tear drop-shaped cross section, the internal diameter (ID) of backing portion 122 in adult-sized devices is in the range of 10 to 15 mm, and the wall thickness may be in the range of 1 to 2 mm.

The portion 132 of gastro-tube 75 proximal of masking ring 55 is integrated with backing portion 122 and is preformed with a generally arcuate longitudinal bend for substantial conformance with curvature of the back of a human tongue where flexed. The proximal end portion 134 of gastro-tube 75, extends outside the patent's mouth and may be connected to gastro-apparatus 137 external of the patent.

Proximal of mask 155, portion 132 may have a concave cut-away portion comprising a curvilinear gutter, shown in cross-section in FIG. 5A that defines an arcuate section closed at its posterior side but open along the anterior side facing the tongue, either substantially throughout the course of the bend or terminating at the level of the distal tip of the uvula. The distal end of the gutter is proximally offset from the bonded posterior tangential contact between gastro-tube 75 and proximal region 65 of masking ring 55. The gutter may preferably be a transversely curved silicone sheet or web, conveniently formed as a proximal prolongation of extending portion 132 which has been longitudinally cut where it emerges proximal to masking ring 55 such that the concave surface of the gutter faces anteriorly. The concave cut-away portion of proximally extending portion 132 and resulting gutter provide a convenient guide for inserting, for example, a small tube through the gastro tube; and also contributes to the flexibility of airway system 20.

Airway Tubes

As indicated above, airway system 20 further comprises a pair of like airway tubes 125, 127 located on opposite sides of, and respectively sealed to and in bonded relation with gastro-tube 75. In preferred embodiments, airway tubes 125, 127 each have a smaller diameter than that of gastro-tube 75. Typically, the interior cross-section area of gastro tube 75 is also at least as large as the combined internal cross sectional areas of airway tubes 125, 127. The inside diameter of each of the airway tubes 125, 127 typically is in the range of 6 to 10 mm, as compared to the 10 to 15 mm inner diameter of gastro tube 75. In devices for adult use, airway tubes 125, 127 typically have an outer diameter of 8 to 10 mm, less than that of the gastro-tube, a wall thickness of 1.25–1.75 mm, and an internal diameter of approximately 7 to 8 mm. Airway tubes 125, 127 are of elastomeric material of durometer hardness in the range 50 to 80; one possible durometer hardness of the material is 70.

It will be recognized that the maximum sizes of the air tubes and gastro tubes are limited by the patient anatomy and the need to provide flexibility; and that the minimum sizes are those required to provide sufficient air flow and permit passage of regurgitated stomach contents. In a typical adult mask, the internal cross-section area of each air tube will be in the range of about 50 to as much as about 80 square mm, and that of the gastro tube will be in the range of about 80 to perhaps as large as about 175 square mm. In the illustrated embodiment, in which the air tubes are 8 mm in internal diameter and the gastro tube has a internal diameter of 10 mm, the total cross-section of the two air tubes is, thus, 100 square mm, about 1.25 times that of the about 80 square mm cross section of the gastro tube.

Airway tubes 125, 127 each have a respective truncated distal end 139, 142 that opens into inner space 57. Since inner space 57 faces laryngeal inlet 50 when masking ring is fully inserted into anatomical airway 22, truncated distal ends 139, 142 communicate with the laryngeal inlet anteriorly on either side of the anteriorly ridged aspect of gastro-tube 75. Each of the truncated distal ends 139, 142 is defined by an elongate slanted truncation with the proximal edge of the truncation of each airway tube being adjacent the top (as viewed in FIG. 1 with mask ring 55 unfolded) of internal space 57 and the distal tip of the truncated distal end approximately midway between the posterior and anterior sides of the inflated tube of masking ring 55. The elongate slanted truncation establishes tapering of distal ends 139, each taper being of reducing arcuate extent in the distal direction, terminating in a distally pointed end. The distal openings of airway tubes 125, 127 are elongate by reason of corresponding diagonally progressive truncations of the airway tubes within the space, into inner space 57, throughout traverse of inner space 57. The lateral border of each taper is curved to match the curve of each inner sidewall of the masking ring.

The portions of the airway tubes 125, 127 adjacent the diagonally-cut medial edges of tapered truncated distal ends 139, 142 are bonded both to the opposite sides of gastro-tube 75 and to the adjacent inner sides of inflatable masking ring 55. Airway tubes 125, 127 are laterally and continuously bonded, e.g. using a hermetic sealant, in side-by-side adjacency to the backing portion 122 of gastro-tube 75 from the distal end to the proximal region 65 of masking ring 55. It will be noted that the bonds between the airway tubes and the masking ring, and also the bonds between the backing portion 122 of gastro tube 75 and the distal and proximal ends of the masking ring, are the equatorial plane of the masking ring, thus insuring that inner space 57 has the desired concavity. It will also be noted that, together, the airway tubes and gastro tube completely close the anterior side of inner space 57.

The bonded-together lateral extent of airway tubes 125, 127 and gastro-tube 75, as viewed in FIG. 2, thus generally forms what is, in effect, a roof over inner space 57 with the truncated distal ends 139, 142 of the airway tubes forming valleys or gutters on either side of the backing portion 122 of gastro-tube. The combined lateral extent or transverse width of backing portion 122 of gastro-tube 75, and airway tubes 125, 127 in masking ring 55 is substantially the transverse width of inner space 57, thereby covering and enclosing the included space within the masking ring. This arrangement eliminates the need for a separate backing plate, as typically used in prior art devices, and the truncated distal ends 139, 142 of airway tubes 125, 127 contribute to the flexibility of the airway system. In the illustrated embodiment, the combined lateral dimension of gastro-tube 75 and airway tubes 125, 127 is between 3 and 3.5 cm.

Proximal to masking ring 55, airway tubes 125, 127 may be secured to proximally extending portion 132 of gastro-tube 75 in continuously bonded relation, similar to manner in which the portions of the airway tubes are bonded to backing portion 122 or to longitudinal portions of the proximally extending portion. If extending portion 132 includes the gutter, described above, the respective airway tubes 125, 127 may be in continuously bonded relation to the respective arcuate limits of the gutter or bonded medially to the gutter. In either construction, such bonding may be accomplished by an adhesive cement 143 such as is shown in FIG. 5. Such an adhesive cement 143 may, though is not required to, provide a hermetic seal.

As shown in FIG. 6, the mask 52 of airway system 20 may optionally include a posterior inflatable pouch or cover 149, the peripheral edge of which is continuously and hermetically bonded to the posterior surface of masking ring 55 and the sections of gastro-tube 75 and airway tubes 125, 127 traversing proximal region 65 of the masking ring. An enclosed space 151 is thereby established between cover 149 and opposing posterior surfaces of masking ring 55, gastro-tube 75 and airway tubes 125, 127. At least one port 153, and preferably a plurality of circumferentially spaced ports 153, are formed in the portion of the, posterior surface of masking ring 55 enclosed by cover 149. Each port 153 provides a fluid flow-path between the interior of masking ring 55 and enclosed space 151, so that inflation of the sealing ring produces concomitant inflation of cover 149 posteriorly relative to the opposed posterior surfaces of masking ring 55, gastro-tube 75 and airway tubes 125, 127. Alternatively, cover 149 may be separately inflatable. In either event, inflating the cover increases the pressure with which the masking ring is urged into sealing engagement around the laryngeal inlet.

Throughout most of its periphery, cover 149 is sealed generally along the center of the top of the inflatable tube of masking ring 55. The proximal portion of cover tapers inwardly, and is bonded to masking ring 55 closely adjacent the sides of airway tubes 126, 127. Tis arrangement prevents possible ballooning of the proximal portion of the cover when it is inflated, and contributes to better sealing. It will also be noted that cover 149 is typically elastomeric, and that the overall unexpanded extent of cover 149 is such that, when it is deflated, the cover conforms closely to the adjacent surfaces of the masking ring, airway tubes and gastro tube, without any folding or creasing of the cover.

Proximal to masking ring 55, airway tubes 125, 127 may be secured to proximally extending portion 132 of gastro-tube 75 in continuously bonded relation, similar to manner in which the portions of the airway tubes are bonded to backing portion 122 or to longitudinal portions of the proximally extending portion. If extending portion 132 includes a gutter, as described above, the respective airway tubes 125, 127 may be in continuously bonded relation to the respective arcuate limits of the gutter or bonded medially to the gutter. In either construction, such bonding may be accomplished by an adhesive cement 143 such as is shown in FIG. 5. Alternatively, the two airway tubes and gastro tube may be extruded or molded as a single unit.

The portions of airway tubes 125, 127 extending proximally from masking ring 55 are generally parallel to each other as they curve away from to the equatorial first plane 67 of sealing ring 55 to exit from the mouth of the patient, and terminate at respective proximal ends proximal of region 65. Alternatively, the portions of airway tubes 125, 127 extending proximally from masking ring 55 may converge to a Y-connection, via a fitment (not shown), externally of the patient, and communicate with a single tube proximal thereof. In either event, the proximal end(s) of the airway tubes may be connected to ventilating apparatus 156.

Other Embodiments

A second embodiment of the lip portion of the gastro tube and the manner in which the lip portion is attached to the backing portion of the gastro tube illustrated in FIGS. 10 through 13. Parts in FIGS. 10 through 13 having a counterpart in FIGS. 2, 3, and 6 to 9 have the same reference numeral with the addition of suffix "a". As shown most clearly in FIG. 12, lip portion tube 77a has a pair of lateral hinges 87, 90 and a pair of medial hinges 92, 95 extending longitudinally in the proximal direction from distal end 80a. Lateral hinges 87, 90 are defined by grooves or cuts that extend through most, but not all, of the radial thickness of lip portion 77a, thus leaving an uncut portion on the base of the inner surface of the lip portion. Medial hinges 92, 95 are defined by grooves that extend through most, but not all, of the radial thickness of lip 77a, similarly leaving an uncut portion as base of the outer surface of the lip portion. Longitudinally of gastro tube 75a, lateral and medial hinges 87, 90, 92, 95 extend proximally from the acute angle edges at the distal end 80a of gastro-tube 75a. Typically lip portion tube 77a has a somewhat greater wall thickness than does the lip portion 77 of the previously discussed embodiment; and lip portion 77a with its hinges 87, 90, 92 and 95 are typically made as a continuous extrusion.

Lateral hinges 87, 90 are symmetrically disposed on opposite sides of lip portion 77a, i.e., on opposite sides of medial second plane 70a. Each lateral hinge 87, 90 is also contained in equatorial first plane 70a. As shown, each lateral hinge 87, 90 is also located approximately in a first plane 70a, at least at the distal end of gastro tube 75. Depending on their length, the proximal portions of each hinge may be inclined posteriorly relative to first plane 70a.

Medial (mid-line) hinges 92, 95 are symmetrically disposed adjacent to the top and bottom of lip portion 77a, on opposite sides of equatorial first plane 70a and circumferentially midway between lateral hinges 87, 90. Each midline hinge 92, 95 is closely adjacent medial second plane 67a. The cross section of lip portion 77a accordingly effectively comprises four equally sized arcuate sections joined by lateral and medial hinges 87, 90, 92, 95.

Figure 13:
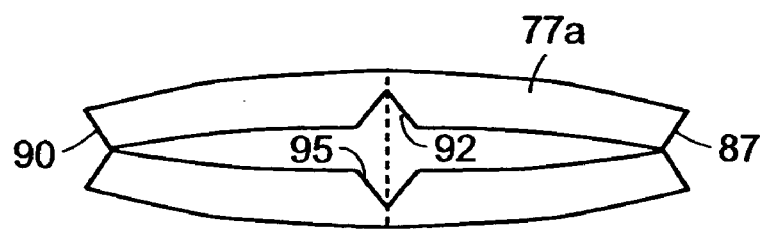
FIG. 13 is an end view of the lip portion of the gastro-tube of FIG. 12, shown in a collapsed condition.
Figure 12:
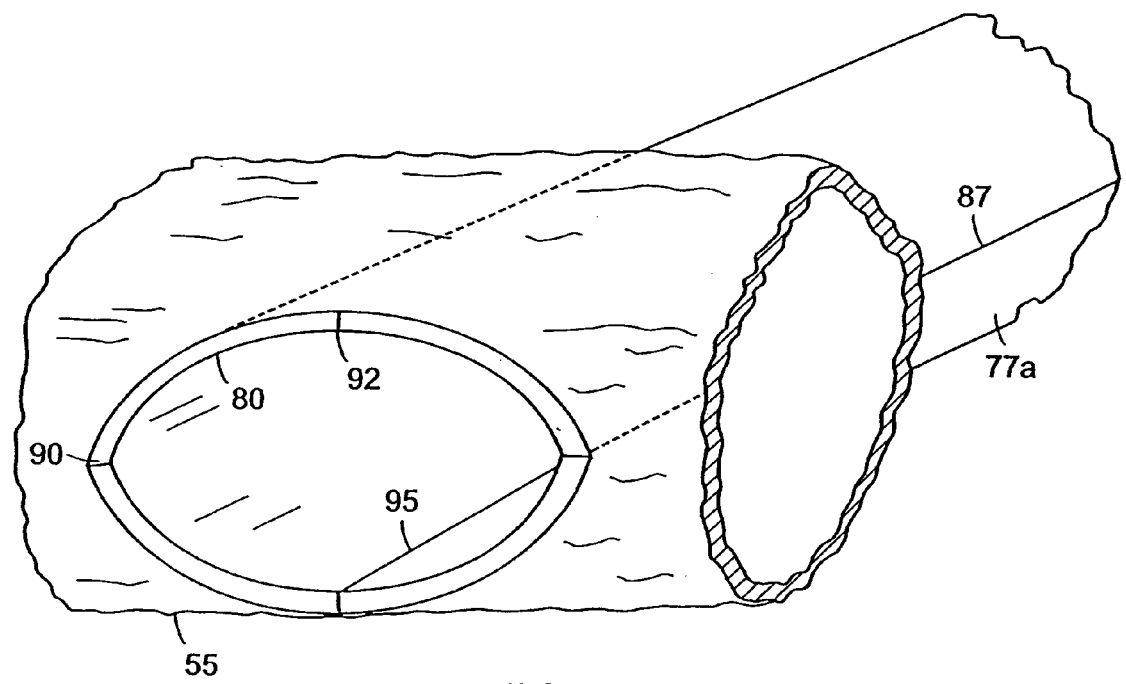
FIG. 12 is an simplified perspective, viewed from the distal end of the alternative embodiment of FIG. 10, of the lip portion of the gastro-tube and the adjacent portions of the masking ring, with the device in the inflated condition.

Flattening of lip portion 77a from the partially expanded condition illustrated in FIG. 12 to the flattened condition shown in FIG. 13 causes pivoting apart of the arcuate sections of the lip portion about the respective lateral and medial hinges 87, 90, 92, 95, as shown in FIG. 13. That is, flattening of lip portion 77a causes widening of the lateral-facing angles of lateral hinges 87, 90, and of the anteriorly and posteriorly facing angles of medial hinges 92, 95. Expanding of lip portion 77a causes reduction of the lateral-facing angles of lateral hinges 87, 90, and of the anteriorly and posteriorly facing angles of medial hinges 92, 95, bringing the edges of the grooves of the respective hinges into juxtaposition with each other. It will be appreciated that lateral and medial hinges 87, 90, 92, 95 are positioned on the inner and outer surfaces of lip portion 77a, respectively, at the points of maximum bending when lip portion 77a is flattened. Accordingly, most of the flexing of the cross section of lip portion 77a required to flatten it is accomplished by flexing lateral and medial hinges 87, 90, 92, 95.

Since the force required to flex the lateral and medial hinges 87, 90, 92, 95 is substantially less than that required to flex the full-thickness portions of lip portion 77a between the hinges, the hinges reduce the radial force required to flatten lip portion 77a from the partially expanded to flattened conditions illustrated in FIGS. 12 and 13. Similarly, the force required to restore lip portion 77a to the partially expanded from the flattened conditions, illustrated in FIGS. 12 and 13, is also reduced. Accordingly, hinges 87, 90, 92, 95 offer low resistance to flexion, thereby causing the lateral-facing walls of gastro-tube 75 to fold or flatten on either side, and lip portion 77a may have a thicker wall thickness as compared to lip portion 77 shown, e.g., in FIGS. 7 and 9, with substantially the same resistance to flattening and expanding.

When lip portion 77a is in its fully expanded configuration, the adjacent side edges of each hinge abut each other. This provides lip portion 77a, when fully expanded, with substantially the same resistance to collapse from externally applied pressure, e.g., pressure from the inflated tube of masking ring 55, as the lip portion would have it were a continuous tube without any hinges.

Figure 10:
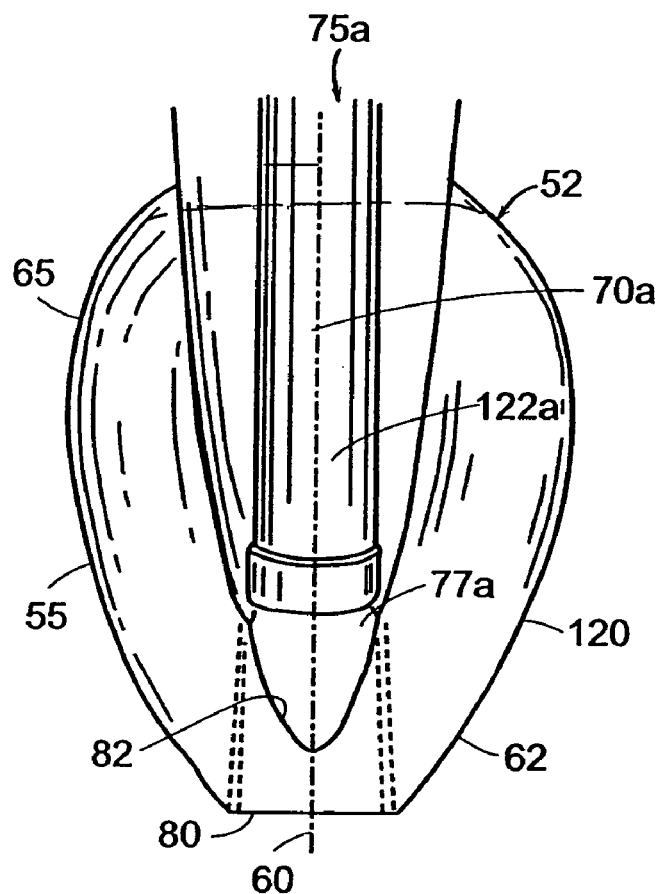
FIG. 10 is a plan view of the posterior side of the alternative embodiment in inflated condition.
Figure 11:
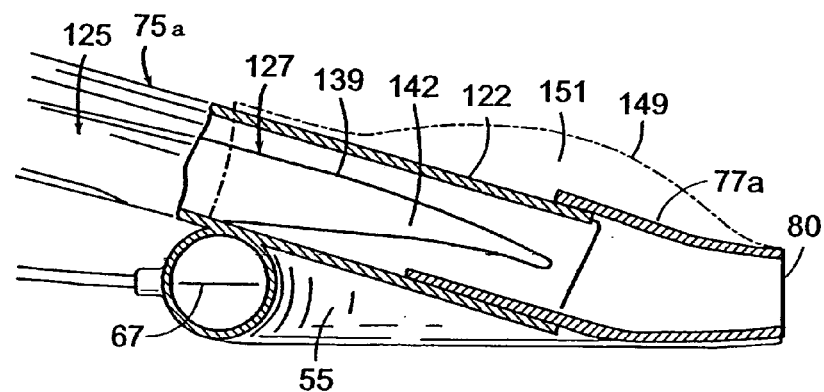
FIG. 11 is a side view in partial section of the alternative embodiment of FIG. 10, in the same plane as that indicated by the line 6—6 of FIG. 3, showing the masking ring and posterior cover in the inflated condition.

With particular reference to FIGS. 10 and 11, it will be seen that the distal end of backing portion 122 of gastro tube 75a is cut perpendicular to the axis of the tube and terminates within the bowl or inner space 57 of masking ring 55. Lip portion tube 77a extends distally into inner space 57 and forms a telescopic joint with the distal end of backing portion 122, to which it is sealed. As in the previously discussed embodiment, the periphery of lip portion tube 77a is bonded to the distal and proximal sides of crotch portion 82 of distal region 62 of masking ring 55.

At the extreme distal end of lip portion 77a, the exterior periphery of the lip portion tube preferably is continuous so as to insure a hermetic seal with the adjacent portion of the inflatable tube of masking ring 55. This may be provided in a number of ways, e.g., additional adhesive may be deposited in the groove of the lateral hinges adjacent the distal end, or the lateral hinges may terminate just short of the distal end. Preferably, the latter is the case and, at the extreme distal end, a short V-shaped groove may be provided on the inside of lip portion 77a in alignment with each of the respective lateral hinges.

Although support plugs, such as plugs 85 in the first described embodiment, may be employed with a hinged lip portion tube 77a, the additional wall thickness of tube 77a typically makes such plugs unnecessary.

OPERATION

In use, an inflation/deflation device attached to tube 72 is actuated to withdraw air from masking ring 55 sufficient fully to deflate it prior to insertion of the mask through the mouth of the patient. Such air withdrawal also deflates cover 149 to collapse it onto the posterior surfaces of gastro-tube 75, airway tubes 125, 127 and masking ring 55 (FIGS. 1 and 8), and air is also withdrawn from distal support plugs 85, resulting in their collapse (FIG. 2).

Lip portion 77 has a relatively lower resistance to flexure, e.g., due to its thin wall thickness throughout its passage through distal region 62 of inflatable/deflatable masking ring 55, and/or because it includes hinges. When masking ring 55 is deflated, lip portion 77 of gastro-tube 75 is flattened in the equatorial first plane 67 of masking ring 55 progressively towards its open distal end 80. As a result, when masking ring 55 is deflated, open distal end 80 and the contiguous part of lip portion 77 of gastro-tube 75 resembles a slit or almost closed fish-mouth shape, as illustrated in FIGS. 9 and 10. Masking ring 55, including lip portion 77, is preferably deflated into a predetermined shape by using the forming tool disclosed in U.S. Pat. No. 5,711,293, the entire disclosure of which is hereby incorporated by reference.

The substantially flattened mask which results when airway device 20 is fully deflated, is passed easily through the mouth of the patient and, by being pressed against hard and soft palates 25, 27 as it is pushed inward, may be guided distally by the soft palate onto the posterior wall of pharynx 30. Deflated masking ring 55 further enters into its correct position opposite laryngeal inlet 50 without colliding with anterior structures such as the posterior surface of the tongue, the epiglottis 45, or the arytenoids. Further disclosure of insertion of deflated airway system 20 through anatomical airway 22 may be had by reference to previously incorporated U.S. Pat. No. 5,632,271, the entire disclosure of which also is hereby incorporated by reference.

Proximally extending portion 132, and preferably backing portion 122, have together sufficient wall thickness to provide a greater resistance to flexure than masking ring 55. The relative stiffness of these portions of gastro-tube 75 enables backing portion 122 and proximally extending portion 132 to pilot or guide the substantially flattened flexible lip of distal region 62 (resulting from a deflated condition of masking ring 55) to smoothly ride or track posterior contours of the throat and pharynx 30 and to assure that the deflated mask or ring is positioned with its distal end located immediately above, and preferably abutting, upper sphincteral region 42 of oesophagus 37, such that the inner space of masking ring 55 overlies and is adjacent to laryngeal inlet 50, as shown in FIG. 1.

Lip portion 77 of gastro-tube 75 and distal region 62 of masking ring 55 are sufficiently flexible to allow anterior and posterior deflection of distal region 62 in medial second plane 70 when the masking ring is fully deflated, as shown in FIG. 8. When the masking ring 55 is deflated, the soft distal end offers less resistance to flexure than the soft palate.

Proximally extending portion 132 extends proximally to the extent of lapped relation with soft palate 27, and may extend proximally to the extent of substantially full lap with the incisor teeth. If a gutter is present, it typically stops short, i.e., distal, of the teeth, and preferably distal to the soft palate, thus permitting nasal passage of tubes into the gastro tube. The region of gastro-tube 75 adjacent hard palate 25 extends upwardly and posteriorly beyond airway tubes 125, 127 such that the combined arrangement of the three tubes fills into the dome of the palate. Airway tubes 125, 127 are spaced inwardly of the sides of the throat at the level of the inner borders of the mandibular bones posteriorly to avoid damage to the lingual nerves.

Gastro-tube 75, if having the gutter described herein above, may form the reception for an introduction tool (not shown) of relatively rigid tubular material having a distal end adapted for insertional guidance in the concavity of the arcuate section of the longitudinal bend of the gutter. The distal end of the introduction tool is further adapted for removably keyed engagement to gastro-tube 75 at the distal end of the gutter. The introduction tool and laryngeal-mask airway system 20 may both be included in a kit.

The introduction tool includes a curved rigid hollow tube with a guiding handle which may be inserted into the gastro-tube 75 at proximal region 65 of masking ring 55, for purposes of facilitating insertion of the masking ring into the patient. Also, the introduction tool may, if required, act as a guide for insertion of a tube into or through gastro-tube 75, for example, in order to drain stomach contents.

When masking ring 55 is correctly positioned, distal end 80 of gastro-tube 75 contacts the upper oesophageal sphincter 40. This is detected by the user as a resistance to insertion of masking ring 55 into oesophagus 37. Masking ring 55 is then inflated with sufficient air, by inflation device 72, to obtain a seal against the laryngo-pharyngeal perimeter. Further disclosure of the manner of positioning masking ring 55 may be had by reference to previously incorporated U.S. Pat. No. 5,241,956.

Inflation of masking ring 55 after the tube had been inserted into the patient up to pressure of approximately 60 cm of water, causes expansion of distal region 62 enabling it to adapt to hypopharynx 32 and upper sphincteral region 42 of oesophagus 37. Inflation of masking ring 55 also causes the gas or fluid supplied to the interior of masking ring 55 to flow through ports 153 into enclosed space 151 resulting in inflation of cover 149, as shown in FIG. 4. Inflation of cover 149 initially causes engagement between the cover and the posterior surface of pharynx 30. This has the advantage of distributing pressure evenly over the surface of the posterior pharyngeal wall, minimizing trauma risk. Further inflation of cover 149 urges masking ring 55 anteriorly to press the masking ring against the tissue surrounding laryngeal inlet 50. This tightens the sealing engagement between masking ring 55 and the tissue surrounding laryngeal inlet 50, thereby reducing leakage between such tissue and the masking ring.

Anteriorly facing inner space 57 of masking ring 55 is normally wider than the transverse distance between the edges of laryngeal inlet 50 as defined by the so-called aryepiglottic folds which bilaterally border the laryngeal inlet, thus encouraging a sealing contact between the ring or cushion and the pharyngeal tissues as well as the tissues bordering the laryngeal inlet. Masking ring 55 is thus functionally a pharyngo-laryngeal mask airway forming an end-to-end seal against larynx 47. If the mask is one in which soft and yielding ridges, as previously discussed, are bilaterally disposed on the anteriorly-facing distal region 62 of masking ring 55, those ridges are suitably contoured to fill the anatomical grooves known as the pyriform fossae to increase the sealing efficacy of masking ring 55. In some embodiments, again as previously discussed, the sealing efficacy of masking ring 55 may be further increased by the optional wedge-shaped crescent in sealing contact with the anterior surface of substantially the proximal one-half of the masking ring.

Epiglottis 45 is supported against a region of gastro-tube 75 in laterally adjacency to and between airway tubes 125, 127. The portion of gastro tube 75 projects in the anterior direction defining a stop to prevent epiglottis 45 of the patient from interfering with communication between airway tubes 125, 127 and laryngeal inlet 50. This stop is provided by the formation of the transverse diameter section of gastro-tube 75, lying within inner space 57 enclosed by masking ring 55, into a roughly pear or tear-drop shape whose pointed end or apex faces anteriorly thus faces toward and in contact with the epiglottis 45. This creates adequate space posterior to epiglottis 45 for passage of gases bilaterally, such that gases passing to and from the trachea 35 are divided into two streams adjacent to gastro-tube 75. The anteriorly-pinched shape in cross section of gastro-tube 75 thus combines with the wider transverse diameter masking ring 55 (i.e., mask or cushion) to permit adequate and free gas communication between the airway tubes 125, 127 and trachea 35, while simultaneously preventing obstruction to such gas flow by epiglottis 45.

Inflation of masking ring 55 expands distal region 62, resulting in bilateral compression of the flattened distal end 80 of gastro-tube 75 and opening lip portion 77, including distal end 80 to the extent permitted by the anatomy abutting the distal end. The flexible material/thin wall thickness of lip portion 77, or hinges illustrated in FIGS. 12 to 13, operates under the influence of pneumatic pressure when air or other fluid is pumped into the closed masking ring to cause distal end 80 of gastro-tube 75 to become less flattened and more nearly circular.

Typically, distal end 80 forms an end-to-end junction with upper esophageal sphincter 40. Thus, the configuration of distal end 80 when mask 55 is inflated may to a significant extent depend on opening and closing of the sphincter. The bilateral compression of flattened distal end 80 causes tube end 80 to tend to assume an oval or roughly circular cross-section; however, this is resisted by the junction between the distal end and the sphincter. However, when sphincter 40 opens as when the patient regurgitates or vomits, it simultaneously permits distal end 80 to open, permitting discharge from the oesophagus to flow into the gastro tube.

The junction between distal end 80 of gastro-tube 75 and distal region 62 of masking ring 55 also provides a seal that obstructs communication between the oesophagus 37 and inner space 57, e.g., leakage of contents from the oesophagus 37 into trachea 35, via inner space 57.

The side-by-side adjacency of gastro-tube 75 and airway tubes 125, 127 prevents kinking of the drainage and airway tubes when they bend around the curved space of oropharynx. Additionally, airway system 20 provides increased flexibility of the artificial airway tubing 125, 127 so that the device is not easily displaced from its sealing engagement both with the oesophagus 37 and larynx 47 by accidental pulling or twisting of the parts of the device external to the patient. Use of a pair of the airway tubes 125, 127 allows a reduced individual tube cross-section diameter while still retaining equal or better gas flow.

After positioning masking ring 55 opposite laryngeal inlet 50 as described herein above, ventilating apparatus 156 is actuated, as needed, to provide anesthesia gas to trachea 35 through airway tubes 125, 127. Separate connection of proximal ends 144, 147 to ventilating apparatus 156 permits a reduction in the so-called "dead space" of the device, which refers to the volume of space enclosed by the device in which gases entering the lungs become mixed with gases emerging from the lungs. This reduction is achieved by arranging for inspired gases to pass into one of the double airway tubes, e.g., 125, while expired gases pass out through the other airway tube, e.g., 127.

Gastro-apparatus 137 may also be actuated, as needed, typically to apply a suction to gastro-tube 75 for drainage or removal of gastric contents from oesophagus 37, or to serve as a guide for passage of tubes into the stomach or oesophagus for drainage, feeding, monitoring or other functions.

An additional internal gastro-tube (not shown) having a smaller OD than the ID of gastro-tube 75 may be telescopically inserted into proximal end 134 of gastro-tube 75. After masking ring 55 has been inserted into upper sphincteral region 42 such that distal end 80 engages upper oesophageal sphincter 40 and the masking ring is fully inflated, the additional gastro-tube may be inserted further into gastro-tube 75 so to emerge from distal end 80 and pass through the upper oesophageal sphincter 40 into oesophagus 37 and subsequently into the stomach thereby facilitating removal of gastric contents.

While this invention has been described with reference to particular devices, other and different devices, including those obvious to those skilled in the art, will embody the invention and are within the scope of the following claims.

What is claimed is:

1. A laryngeal mask airway device, including:
   A. at least one airway tube having a proximal end and a distal end;
   B. a drainage tube having a proximal end and a distal end;
   C. a mask portion coupled to the airway tube and the drainage tube, the mask portion including an inflatable cuff, the mask portion being insertable through a mouth of a patient to an inserted location within the patient, the cuff surrounding a glottic opening of the patient when inflated and when the mask portion is at the inserted location, a sealed airway passage extending from the proximal end of the airway tube to the glottic opening when the cuff is inflated and when the mask portion is at the inserted location, the distal end of the drainage tube contacting an oesophageal inlet of the patient when the mask portion is at the inserted location, the distal end of the drainage tube being in a first position when (i) the mask portion is at the inserted location, (ii) the mask portion is inflated, and (iii) the oesophageal inlet is closed, the distal end of the drainage tube being in a second position when (i) the mask portion is at the inserted location, (ii) the mask portion is inflated, and (iii) the esophegeal inlet is open, an area of an opening at the distal end of the drainage tube being greater when the distal end of the drainage tube is in the second position than when in the first position.

2. The laryngeal mask airway device of claim 1, wherein the at least one airway tube comprises two airway tubes.

3. The laryngeal mask airway device of claim 1, wherein a distal portion of the drainage tube extends through a distal portion of the inflatable cuff.

4. The laryngeal mask airway device of claim 1, wherein the mask portion is collapsible for insertion into the inserted location within the patient, a distal portion of the drainage tube being closed during insertion.

5. The laryngeal mask airway device of claim 1, wherein a distal portion of the drainage tube has a pair of hinges positioned on generally opposite sides of the drainage tube, each of the hinges extending generally longitudinally along the drainage tube.

6. The laryngeal mask airway device of claim 5, wherein the hinges are defined by the radial thickness of the drainage tube.

7. The laryngeal mask airway device of claim 1, further including a pair of collapsible support plugs disposed within a distal portion of the inflatable cuff, one on each side of the drainage tube.

\* \* \* \* \*